United States Patent [19]
Trebosc et al.

[11] Patent Number: 4,938,962
[45] Date of Patent: Jul. 3, 1990

[54] HETEROGENEOUS TOPICAL COMPOSITIONS HAVING A BASE OF MICROGRANULES OF CAFFEINE AND/OR ITS DERIVATIVES, WHICH CAN BE USED AS SLENDERIZER AND/OR IN THE TREATMENT OF CELLULITIS, AS WELL AS THEIR PREPARATION

[75] Inventors: Marie-Thérese Trebosc; Henri Cousse, both of Castres; Gilbert Mouzin, Toulouse, all of France

[73] Assignee: Pierre Fabre Cosmetique, Paris, France

[21] Appl. No.: 281,082

[22] Filed: Dec. 7, 1988

[30] Foreign Application Priority Data

Dec. 7, 1987 [FR] France .................. 87 16969

[51] Int. Cl.$^5$ .............................. A61K 47/00
[52] U.S. Cl. .................. 424/439; 424/489; 424/490
[58] Field of Search ........... 424/490, 489, 439, 451; 514/944

[56] References Cited

U.S. PATENT DOCUMENTS

| | | | |
|---|---|---|---|
| 3,084,104 | 4/1963 | Tuerck et al. | 167/82 |
| 4,698,264 | 10/1987 | Steinke | 514/963 X |
| 4,762,707 | 8/1988 | Gergely et al. | 424/489 X |

*Primary Examiner*—Thurman K. Page
*Attorney, Agent, or Firm*—Gordon W. Hueschen

[57] ABSTRACT

The present invention relates to a heterogeneous topical composition comprising microgranules or microparticles of a topically-acceptable caffeine metal carboxylate in a hydroalcoholic gel, as well as its preparation and use. The composition, which can be used as slenderizer and/or in the treatment of cellulitis, comprises a long acting topically-acceptable caffeine metal carboxylate as the active principle, which is present in the form of heterogeneously-distributed microgranules or microparticles, having a diameter of about 0.2 to 2 millimeters, suspended in a hydroalcoholic gel in which they are insoluble, advantageously together with Vitamin E or a derivative thereof.

18 Claims, No Drawings

HETEROGENEOUS TOPICAL COMPOSITIONS HAVING A BASE OF MICROGRANULES OF CAFFEINE AND/OR ITS DERIVATIVES, WHICH CAN BE USED AS SLENDERIZER AND/OR IN THE TREATMENT OF CELLULITIS, AS WELL AS THEIR PREPARATION

BACKGROUND OF INVENTION AND PRIOR ART

The present invention, which originates from the PIERRE FABRE Dermatological and Cosmetological Center, relates to new cosmetic formulations in which the active principle or principles are present in heterogeneous suspension within a hydroalcoholic gel in the form of microgranules or microparticles.

The active principle consists essentially of a long-acting caffeine metal carboxylate, advantageously in combination with Vitamin E or a derivative thereof.

According to the state of the prior art, slenderizing preparations consisted of hydroalcoholic translucent gels of homogeneous appearance. In accordance with the present invention, the entirely new and long-acting active principle is visualized, i.e., appears, in the slenderizing composition in the form of heterogeneously-distributed microgranules or microparticles which are totally insoluble or at best relatively insoluble, i.e., poorly soluble, in the hydroalcoholic gel.

OBJECTS OF THE INVENTION

It is an object of the present invetnion to provide new and improved topical compositions for use in slenderizing and in the treatment of cellulitis, such compositions which contain novel and long-acting principles which are topically- and cosmetically-acceptable caffeine metal carboxylates, which principles are heterogeneously-distributed throughout a hydroalcoholic gel in which they are insoluble, and a method of preparing the same. Other objects of the invention will be obvious to one skilled in the art and still others will become apparent upon reading the following specification and claims.

SUMMARY OF THE INVENTION

The present invention, then, comprises the following aspects, inter alia, alone or in combination:

a heterogeneous topical composition which can be used as slenderizer or in the treatment of cellulitis, characterized in that it comprises, as active principle, a topically-acceptable caffeine metal carboxylate, said active principle being present in the form of microgranules or microparticles, having a diameter of about 0.2 to 2 millimeters, which are heterogeneously-distributed and suspended in a hydroalcoholic gel in which they are insoluble, such composition wherein the microgranules or microparticles have a diameter between about 0.4 and 1 millimeter; such composition wherein the microgranules or microparticles are present in an amount between about 0.5 and 20 percent by weight of the total composition; such composition wherein the microgranules or microparticles are present in an amount between about 1 and 10 percent by weight of the total composition, such composition wherein the individual particles comprising the microgranules or microparticles are of an average size between about 5 and 20 microns in diameter, such composition wherein the individual particles comprising the microgranules or microparticles are of an average size between about 5 and 15 microns in diameter, such composition characterized in that the caffeine metal carboxylate is zinc caffeine carboxylate, magnesium caffeine carboxylate, aluminum caffeine carboxylate, calcium caffeine carboxylate, and such composition which also contains Vitamin E or a derivative thereof.

Moreover, a method of preparing microparticles or microgranules containing as active principle a topically-acceptable caffeine metal carboxylate, comprising the following steps, steps (a) and (c) being optional:

(a) a solid inert binder support is micronized until scales of an average size less than 50 microns are obtained, (b) particles impreganated with active principle or particles of the active principle itself are micronized until particles of an average size less than 50 microns are obtained, (c) the scales when obtained in step (a) are mixed with the particles obtained in step (b)

(d) a wetting agent is added; the product from step (b) or (c) is agglomerated and the agglomerated product is dried to produce a powder which, after drying, is screened to form microgranules or microparticles of about 0.2 to 2 millimeters in diameter, such method wherein the microgranules or microparticles are between about 0.4 and 1 millimeter in diameter, such method wherein the particles in step (a) when present and step (b) are micronized to an average size between about 5 and 20 microns in diameter, such method wherein the particles in step (a) when present and step (b) are micronized to an average size between about 5 and 15 microns in diameter, such method wherein the wetting agent is a lower alcohol, such method wherein the wetting agent is ethanol, such method wherein the microgranules or microparticles are heterogeneously mixed into a hydroalcoholic gel in which they are insoluble, such method wherein the microgranules or microparticles are mixed into the gel in an amount of about 0.5 to 20 percent by weight of the total composition, such method wherein the microgranules or microparticles are mixed into the gel in an amount of about 1 to 10 percent by weight of the total composition, and such method wherein the caffeine metal carboxylate is the caffeine zinc, magnesium, aluminum, or calcium carboxylate.

DESCRIPTION OF INVENTION

The active principle used in the present invention is a caffeine metal carboxylate of general Formula (I):

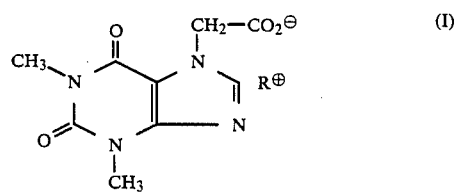

in which:

$R^+$ represents the cation of a topically- or cosmetically-acceptable metal, especially zinc, magnesium, aluminum, or calcium.

The preparation of the new active principle used in the compositions of the present invention and the compositions themselves is illustrated by the Preparations and Examples which follow, which are given by way of illustration only and are not to be construed as limiting.

PREPARATION OF ACTIVE PRINCIPLE

EXAMPLE 1

Preparation of zinc caffeine carboxylate 238.2 g (1 mol) of caffeine carboxylic acid are solubilized in one liter of caustic soda (N), with agitation. To the orange-colored, clear solution there are added 143.7 g (0.5 mol) of hydrated zinc sulphate dissolved in 150 ml of water. It is set aside with strong agitation for one hour. A white precipitate forms; after filtration and drying, the product of the formula is recovered quantitatively.

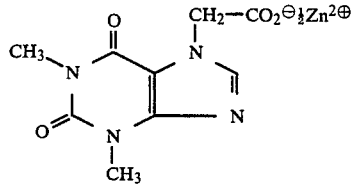

Empirical formula: $C_{18}H_{18}N_8O_8Zn$; MW: 539.76
Physico-chemical characteristics
Color: White; Melting point > 260° C.
Elementary analysis (Lot FII 137)

| | C | H | N | Zn |
|---|---|---|---|---|
| Calculated | 40.05 | 3.36 | 20.76 | 12.11 |
| Found | in agreement with 28.8% water | | | |

Thin-layer chromatography:
Silica gel 60 F 254 MERCK; Ref.: 0.68
Solvent: Chloroform-methanol 50:50
Visualization: UV Solubilities Water: 0.1%; Ethanol at 30° C. insoluble
Peanut oil: insoluble.

The following products were prepared in a manner similar to that described in Example 1.

EXAMPLE 2

Magnesium caffeine carboxylate

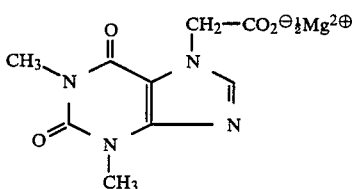

Empirical formula: $C_{18}H_{18}N_8O_8Mg$; MW: 498.71
Physico-chemical characteristics
Color: White; Melting point > 260° C.
Elementary analysis (Lot FII 135)

| | C | H | N | Mg |
|---|---|---|---|---|
| Calculated | 43.35 | 3.64 | 22.47 | 4.87 |
| Found | in agreement with 34% water | | | |

Thin-layer chromatography:
Silica gel 60 F 254 MERCK; Ref.: 0.68
Solvent: $CHCl_3$ - MeOH 50:50
Visualization: UV Solubilities Water: 0.5%; Ethanol 0.5%
Peanut oil: insoluble.

EXAMPLE 3

Aluminum caffeine carboxylate

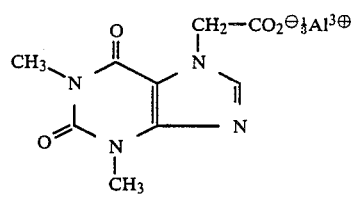

Empirical formula: $C_{27}H_{27}N_{12}O_{12}Al$; MW: 738.57
Physico-chemical characteristics
Color: White; Melting point > 260° C.
Elementary analysis (Lot FII 150)

| | C | H | N | Al |
|---|---|---|---|---|
| Calculated | 43.12 | 3.62 | 22.35 | 5.38 |
| Found | in agreement with 13.4% water | | | |

Thin-layer chromatography:
Silica gel 60 F 254 MERCK; Ref.: 0.68
Solvent: $CHCl_3$ - MeOH 50:50
Visualization: UV Solubilities Water: 3%; Ethanol 30° C.: 1%
Peanut oil: insoluble.

EXAMPLE 4

Calcium caffeine carboxylate

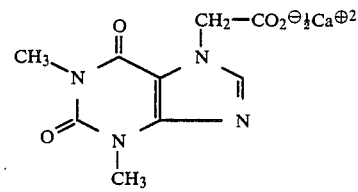

Empirical formula: $C_{18}H_{18}N_8O_8Ca$; MW: 550.48
Physico-chemical characteristics
Color: White; Melting point > 300° C.
Elementary analysis (Lot AXXI 121)

| | C | H | N | Ca |
|---|---|---|---|---|
| Calculated | 39.27 | 4.03 | 20.35 | 7.28 |
| Found | in agreement with 7.3% water | | | |

Thin-layer chromatography:

Silica gel 60 F 254 MERCK; Ref.: 0.68
Solvent: CHCl$_3$ - MeOH 50:50
Visualization: UV Solubilities Water: 2%; Ethanol 30° C.: 1%
Peanut oil: insoluble.

Other caffeine metal carboxylates are prepared in the same manner.

In accordance with the present invention, the heterogeneous galenic preparations for cosmetic use contain, as active principle, a derivative of caffeine having the general Formula I, whether or not associated with Vitamin E or a derivative thereof, the said active principle being present in the form of microgranules, microparticles, or similar entities which are insoluble or very difficultly soluble in the base hydroalcoholic gel.

The active principle is thus liberated progressively over an extended period of time upon topical application.

Such a prolonged liberation is obtained due to the unique active principle itself and due to its preparation into heterogeneous particles or granules which usually comprise at least two solid phases, namely, a solid inert binder and the active principle.

The first phase comprises a solid inert binder support, and the second phase comprises particles impregnated with active principle and/or particles of essentially pure active principle itself.

The preparation of such gel formulations of the invention entails the following:

A method of preparing particles or granules containing as active principle a topically-acceptable caffeine metal carboxylate, comprising the following steps, steps (a) and (c) being optional:

(a) the first phase comprising the solid inert binder support is micronized until scales having an average size less than 50 microns are obtained, (b) the charge particles impregnated with active principle or particles of the active principle itself are micronized until particles having an average size less than 50 microns are obtained, both (a) and (b) preferably being reduced to an average particle size between about 5 and 20 microns in diameter, especially 5 to 15 microns in diameter, (c) the scales when obtained in step (a) are mixed with the particles obtained in step (b), (d) a wetting agent such as ethanol or other loweralkanol is added; the product from step (b) or (c) is agglomerated and the agglomerated product is dried to produce a powder which, after drying and ventilation, is sieved or screened to form granules or particles having a particle size of about 0.2 to 2 millimeters in diameter, preferably between about 0.4 and 1 millimeter in diameter, whereafter the thus-produced microgranules or microparticles are heterogeneously mixed into a hydroalcoholic gel in which they are insoluble, the microgranules or microparticles being mixed into the gel in an amount of about 0.5 to 20 percent by weight of the total composition, preferably in an amount of about 1 to 10 percent by weight of the total composition.

The microparticles of the pure active principle or the microparticles charged with microgranulated active principle in accord with the present invention are:

a topically and/or cosmetically-acceptable caffeine metal carboxylate, e.g., zinc caffeine carboxylate, magnesium caffeine carboxylate, aluminum caffeine carboxylate, or calcium caffeine carboxylate, if desired combined with a vitamin and especially with Vitamin E and/or a derivative thereof.

The gel formulations of the invention contain about 0.5 to 20% w/w, preferably 1 to 10% w/w, of microgranules charged with active principle or microparticles of pure active principle itself in a suitable base comprising cosmetic excipients in the form of a hydroalcoholic gel, usually of a transparent or preferably translucent nature, in a manner known to one skilled in the art. The base is, however, selected so that the particles are totally or essentially insoluble therein.

By way of nonlimitative Examples, particular mention may be made of hydroalcoholic gel slenderizing formulations, preferably containing about 1 to 10% w/w microgranules or microparticles having the following compositions:

MICROPARTICLE OR MICROGRANULE FORMULATIONS (each ingredient micronized to less than 50 microns in diameter, preferably to an average particle size of 5-20 microns and especially 5-15 microns in diameter)

| Example 1 Microgranules | |
|---|---|
| aluminum caffeine carboxylate | 50 to 70% |
| Starch | 20 to 30% |
| Ethyl cellulose | 5 to 20% |
| Example 2 Microparticles | |
| Zinc caffeine carboxylate | 100% |
| Example 3 Microparticles | |
| Zinc caffeine carboxylate | 60 to 70% |
| Vitamin E | 30 to 40% |
| Example 4 Microgranules | |
| Magnesium caffeine carboxylate | 50 to 80% |
| Starch | 20 to 50% |
| Example 5 Microgranules | |
| Calcium caffeine carboxylate | 50 to 70% |
| Vitamin E | 20 to 30% |
| Starch | 5 to 20% |

The microparticles and/or microgranules are treated with a wetting agent, the wetted mass agglomerated into larger particles and/or granules, the particles or granules dried to form a powder, and the powder sieved or screened to provide microgranules or microparticles having an average particle size of about 0.2 to 2 millimeters, preferably about 0.4 to 1 millimeter, in diameter.

Finally, the caffeine metal carboxylate microparticles or microgranules are combined into and heterogeneously distributed in the hydroalcoholic gel by simple careful introduction and admixture into the gel composition, according to the skill of the art, a representative final gel composition having the following illustrative ingredients and proportions:

FINAL HYDROALCOHOLIC GEL COMPOSITION

| Example 1 | |
|---|---|
| Algae extract (agar) | 1 to 5% by weight |
| 95° ethanol (or other non-toxic alcoholic compound) | 10 to 30% |

| Example 1 | |
|---|---|
| Carboxyvinyl polymer (or other polymeric support) | 0.3 to 1% |
| Triethanolamine | 3 to 10% |
| Microgranules or microparticles according to any of Examples 1 to 5 | 0.5 to 20% (preferably 1 to 10%) |
| Softened (demineralized) water | qsp 100% w/w |

The insoluble or nearly-insoluble microgranules or microparticles are randomly and heterogeneously distributed throughout the translucent gel by stirring thereinto. The product is used by applying it to the area to be slenderized, or to the area in which cellulitis is to be reduced or eliminated, and rubbing it in, according to conventional practice in the art.

VARIATIONS IN COMPOSITIONS AND RANGES

A. Inert Binder Support

Examples of other suitable materials are polymeric materials and especially thermoplastic polymeric materials such as ethylcellulose, ethylhydroxycellulose, hydroxypropylcellulose, carboxymethylcelluloses, and despolyvinylpyrrolidones.

B. Range of Starting Microgranule or Microparticle Ingredient Diameters

Less than 50 microns, preferably 5 to 20 microns, advantageously 5–15 microns.

C. Range of Final Microgranule or Microparticle Diameters

Average particle diameter of about 0.2 to 2 millimeters, preferably about 0.4 to 1 millimeter.

D. Wetting agent

A lower-alcohol, preferably a lower-alkanol such as ethanol, methanol, propanol, or isopropanol, ethanol being preferred.

E. The Gel Formulation

The formulations contain about 0.5 to 20% w/w of microgranules or microparticles on a basis of the total composition including the hydroalcoholic gel, and preferably contain about 1 to 10% w/w of microgranules or microparticles on a basis of the total composition including the hydroalcoholic gel.

The heterogeneous caffeine metal carboxylate gel formulations of the present invention are tolerated well. They place in action soft microgranules or microparticles which do not involve the intervention of any inorganic agent which could be considered a foreign body.

In accord with the present invention, the formulations prepared on a basis of the presence, as active principle, of a caffeine metal carboxylate, have excellent and long-acting "lipolytic" properties and have therefore proven very effective in slenderizing programs and in the treatment of cellulitis.

In conclusion, from the foregoing, it is apparent that the present invention provides novel heterogeneous topical compositions useful for slenderizing and/or in the treatment of cellulitis, involving the local or topical application thereof, in which novel topical compositions a topically or cosmetically-acceptable caffeine metal carboxylate is present in the form of soft heterogeneously-distributed microgranules or microparticles in a topically-acceptable hydroalcoholic gel carrier or diluent, in which they are insoluble, all having the foregoing enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

What is claimed is:

1. Heterogeneous topical composition which can be used as slenderizer or in the treatment of cellulitis, characterized in that it comprises, as active principle, a caffeine metal carboxylate selected from zinc, magnesium, aluminum, and calcium caffeine carboxylates, said active principle being present in the form of microgranules or microparticles, having a diameter of about 0.2 to 2 millimeters, which microgranules or microparticles are present in an amount between about 0.5 and 20 percent by weight of the total composition and which are heterogeneously-distributed and suspended in a gel comprising water and a nontoxic alcohol in which they are insoluble.

2. Composition of claim 1 wherein the microgranules or microparticles have a diameter between about 0.4 and 1 millimeter.

3. A composition of claim 1, wherein said composition also contains Vitamin E.

4. Composition of claim 1 wherein the microgranules or microparticles are present in an amount between about 1 and 10 percent by weight of the total composition.

5. Composition of claim 1 wherein the individual particles comprising the microgranules or microparticles are of an average size between about 5 and 20 microns in diameter.

6. Composition of claim 1 wherein the individual particles comprising the microparticles or microgranules are of an average size between about 5 and 15 microns in diameter.

7. A composition according to claim 1, characterized in that the caffeine metal carboxylate is zinc caffeine carboxylate.

8. A composition according to claim 1, characterized in that the caffeine metal carboxylate is magnesium caffeine carboxylate.

9. A composition according to claim 1, characterized in that the caffeine metal carboxylate is aluminum caffeine carboxylate.

10. A composition according to claim 1, characterized in that the caffeine metal carboxylate is calcium caffeine carboxylate.

11. A method of preparing microparticles or microgranules containing as active principle a caffeine metal carboxylate selected from zinc, magnesium, aluminum, and calcium caffeine carboxylates, comprising the following steps, steps (a) and (c) being optional:
  (a) a solid inert binder support is micronized until scales of an average size less than 50 microns are obtained,
  (b) particles impregnated with active principle or particles of the active principle itself are micronized until particles of an average size less than 50 microns are obtained, (c) the scales when obtained in step (a) are mixed with the particles obtained in step (b)

(d) a wetting agent is added; the product from step (b) or (c) is agglomerated and the agglomerated product is dried to produce a powder which, after drying, is screened to form microgranules or microparticles of about 0.2 to 2 millimeters in diameter.

12. Method of claim 11 wherein the microgranules or microparticles are heterogeneously mixed into a gel comprising water and a nontoxic alcohol in which they are insoluble in an amount of about 0.5 to 20 percent by weight of the total composition.

13. Method of claim 11 wherein the microgranules or microparticles are between about 0.4 and 1 millimeter in diameter.

14. Method of claim 11 wherein the particles in step (a) and step (b) are micronized to an average size between about 5 and 20 microns in diameter.

15. Method of claim 11 wherein the particles in step (a) and step (b) are micronized to an average size between about 5 and 15 microns in diameter.

16. Method of claim 11 wherein the wetting agent is a lower alkanol.

17. Method of claim 11 wherein the wetting agent is ethanol.

18. Method of claim 12 wherein the microgranules or microparticles are mixed into the gel in an amount of about 1 to 10 percent by weight of the total composition.

* * * * *